(12) United States Patent
Ichikawa et al.

(10) Patent No.: US 9,480,607 B2
(45) Date of Patent: Nov. 1, 2016

(54) PANTS-TYPE WEARING ARTICLE

(71) Applicant: Unicharm Corporation, Ehime (JP)

(72) Inventors: Makoto Ichikawa, Kanonji (JP); Nobuhiro Tagawa, Kanonji (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 14/420,216

(22) PCT Filed: Oct. 10, 2012

(86) PCT No.: PCT/JP2012/076171
§ 371 (c)(1),
(2) Date: Feb. 6, 2015

(87) PCT Pub. No.: WO2014/024326
PCT Pub. Date: Feb. 13, 2014

(65) Prior Publication Data
US 2015/0223994 A1 Aug. 13, 2015

(30) Foreign Application Priority Data

Aug. 7, 2012 (JP) ................................. 2012-175438
Aug. 28, 2012 (JP) ................................. 2012-188064

(51) Int. Cl.
| | |
|---|---|
| A61F 13/539 | (2006.01) |
| A61F 13/496 | (2006.01) |
| A61F 13/515 | (2006.01) |

(52) U.S. Cl.
CPC ........... *A61F 13/496* (2013.01); *A61F 13/515* (2013.01); *A61F 13/539* (2013.01)

(58) Field of Classification Search
CPC ............... A61F 13/49061; A61F 2013/49063; A61F 2013/49065; A61F 13/515; A61F 13/539; A61F 13/49058; A61F 13/4906
See application file for complete search history.

(56) References Cited

U.S. PATENT DOCUMENTS

| | | | | |
|---|---|---|---|---|
| 2004/0166756 A1* | 8/2004 | Kurihara | ................. | B29C 43/28 442/366 |
| 2005/0288648 A1* | 12/2005 | Otsubo | ............. | A61F 13/49001 604/385.201 |
| 2008/0161768 A1* | 7/2008 | Baba | ................. | A61F 13/15593 604/385.27 |

FOREIGN PATENT DOCUMENTS

| | | |
|---|---|---|
| JP | 2002-320641 | 11/2002 |
| JP | 2005-027839 | 2/2005 |
| JP | 2008-212232 | 3/2008 |
| JP | 2012-024463 | 2/2012 |
| WO | WO 2008/078610 A1 | 7/2008 |

OTHER PUBLICATIONS

Translation of JP2002320641.*
International Search Report from corresponding PCT application No. PCT/JP2013/076171 dated Dec. 11, 2012 (4 pgs).

* cited by examiner

*Primary Examiner* — Peter S Vasat
(74) *Attorney, Agent, or Firm* — Brinks Gilson & Lione

(57) ABSTRACT

A pants-type wearing article in which at least a central segment of a crotch region has a desired degree of flexibility and a portion of a crotch region close to a front waist region has a desired degree of tensile strength. The front and rear waist regions and at least a portion of the crotch region close to the front waist region define a multilayer zone composed of a base sheet and a front waist sheet layered with each other and a central segment of the crotch region defines a monolayer zone formed of the base sheet alone. The multilayer zone includes corners each surrounded by a boundary, an inner end of the front waist region, a joint region in which a liquid-absorbent structure is bonded to a chassis and a concave lateral edge of the crotch region and the boundary extends across the joint region.

20 Claims, 9 Drawing Sheets

PANTS-TYPE WEARING ARTICLE

RELATED APPLICATION

This application is a 35 U.S.C. §371 national phase filing of International Patent Application No. PCT/JP2012/076171, filed Oct. 10, 2012, through which and to which priority is claimed under 35 U.S.C. §119 to Japanese Patent Application Nos. 2012-175438, filed Aug. 7, 2012 and 2012-188064, filed Aug. 28, 2012, the complete disclosures of which are hereby expressly incorporated herein by reference.

TECHNICAL FIELD

The present invention relates to pants-type wearing articles such as disposable pants-type diapers and incontinent diaper covers.

BACKGROUND

Conventionally, wearing articles composed of the chassis defining the basic form of the pants-type wearing article and the liquid-absorbent structure lying on the inner surface of the chassis is known. For example, a wearing article disclosed by JP 2005-27839 A (PTL 1) is composed of a chassis including a transversely long rectangular shaped front waist panel and a substantially trapezoidal shaped rear waist panel defining a rear waist region and part of a crotch region and a liquid-absorbent structure lying on the inner surface of the chassis. In such wearing article, the front and rear waist panels are respectively provided with a plurality of waist elastics extending in a transverse direction and an extension segment of the rear waist panel defining part of the crotch region are provided with a plurality of leg-elastics.

CITATION LIST

Patent Literature

{PTL 1}: JP 2005-27839 A

SUMMARY

Technical Problem

In the wearing article disclosed in PTL 1, any sheet member constituting the chassis is not present in a central segment of the crotch region extending between the front waist panel and rear waist panel, and only the liquid-absorbent structure is present in this central segment. With such an arrangement, the article is superior to the article including a plurality of sheet members constituting the chassis in the central segment of the crotch region so far as the flexibility is concerned. In consequence, even when the central segment of the crotch region is wedged between the wearer's thighs and folded, the folded central segment is unlikely to become rough and to affect the feeling to wear. Also, none of the sheet members constituting the chassis is arranged in the central segment of the crotch region, so that the manufacturing cost can be reduced.

However, there is a problem due to a fact that, when the wearing article is put on the wearer's body, lateral edges of the liquid-absorbent structure and portions in the vicinity thereof which extend rectilinearly are necessarily kept in contact with curved surfaces of the wearer's thighs. Specifically, when the wearer or a care person holds lateral portions of the front and rear waist regions and pulls up the wearing article during or after insertion of the wearer's legs into the leg-openings by the wearer or the care person, there is a likelihood that part of the liquid-absorbent structure lying in the crotch region close to the front waist region might be caught by inner sides of the thighs and peripheries of the respective leg-openings might be forcibly extended in a vertical direction. In such situation, a tensile stress developing along the peripheries of the leg-openings is concentrated in regions in which the respective peripheries are most deformed, namely, in the regions in which a lower end of the front waist panel rectilinearly extending in a transverse direction intersects with lateral edges of the liquid-absorbent structure rectilinearly extending in a longitudinal direction. As a result, there is a likelihood that the wearing article might be partially broken in the vicinity of the intersecting portions. Additionally, in such a wearing article in which the front and rear waist regions and the crotch region are formed of separate sheet members, the separate sheet members might be peeled off from each other along the joint line when the waist regions and/or the crotch region are pulled.

To avoid such situation, it may be contemplated to constitute the entire wearing article inclusive of the crotch region to improve a sheet strength of the chassis as a whole. In this case, however, the flexibility of the crotch region in the central segment thereof will be deteriorated and the increased quantity of the sheet members to be used will increase the manufacturing cost.

An object of the present invention is to provide a disposable wearing article in which at least the central segment of the crotch region has a desired degree of flexibility and the portion of the crotch region close to the front waist region has a desired degree of tensile strength.

Solution to Problem

The present invention relates to a pants-type wearing article having a longitudinal direction and a transverse direction being orthogonal to the longitudinal direction, and including a skin-facing surface, a non-skin-facing surface, a front waist region, a rear waist region, a crotch region extending between the front and rear waist regions and having concave lateral edges, a chassis defining the front and rear waist region and the crotch region, and a liquid-absorbent structure affixed on the side of the skin-facing surface to the chassis and extending in the longitudinal direction at least in the crotch region.

The wearing article according to the present invention further includes the following features:

the chassis includes a base sheet defining the front and rear waist regions and the crotch region and front and rear waist sheets spaced apart from each other in the longitudinal direction and defining together with the base sheet the front and rear waist regions;

the front and rear waist regions and at least a portion of the crotch region close to the front waist region define a multilayer zone composed of the base sheet and the front waist sheet layered with each other and a central segment of the crotch region defines a monolayer zone formed of the base sheet alone;

a boundary between the multilayer zone and the monolayer zone extends in the transverse direction, and the multilayer zone includes corners each surrounded by the boundary, an inner end of the front waist region, a joint region in which the liquid-absorbent structure is affixed to the chassis and the concave lateral edge of the crotch region, wherein the boundary extends across the joint region.

Advantageous Effects of Invention

In the pants-type wearing article according to the present invention, the base sheet constituting the chassis extends entirely over the front and rear waist regions and the crotch region and, in contrast to where the crotch region is formed of the sheet prepared separately from the sheet for the front and rear waist regions, the crotch region might be readily peeled off from the front and rear waist regions even if these regions pulled in the longitudinal direction during use of the article. As an additional unique arrangement, the chassis includes, in the portion of the crotch region close to the front waist region, the multilayered corners defined between the joint region in which the liquid-absorbent structure is joined to the chassis and the concave lateral edges of the crotch region. These corners have a sufficiently high tensile strength and high load-deconcentrating properties to prevent the leg-opening peripheries from being partially broken even if the force acting to pull up in the longitudinal direction is exerted on the leg-opening peripheries during use of the article. Further, the central segment of the crotch region is formed of the base sheet alone and, in consequence, has an adequate flexibility whereby the wearer's skin should not be irritated and the central segment should not become rough even when this segment is squeezed between the wearer' thighs. In this way, the comfortable feeling to wear can be ensured.

DESCRIPTION OF EMBODIMENTS

Figure 1:
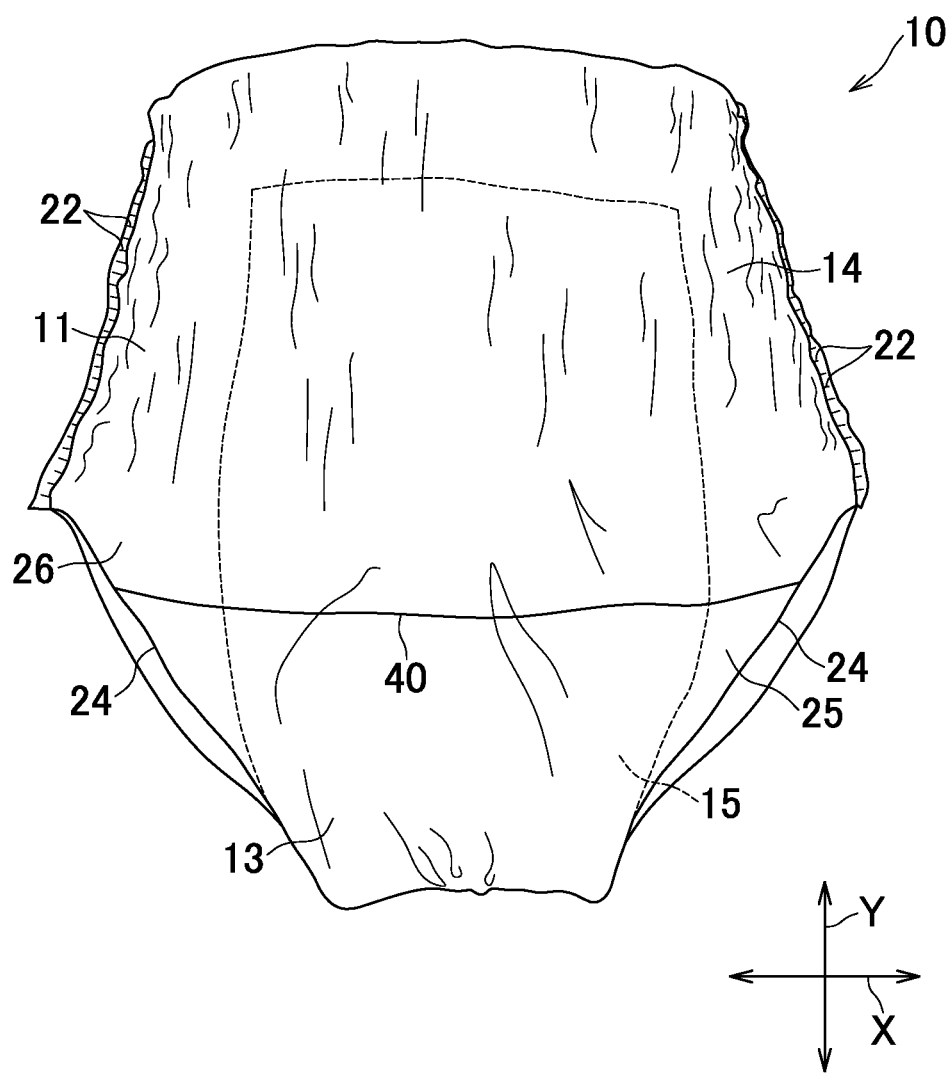
FIG. 1 is a perspective view of a disposable pants-type diaper as one example of the pants-type wearing article according to the present invention.
Figure 2:
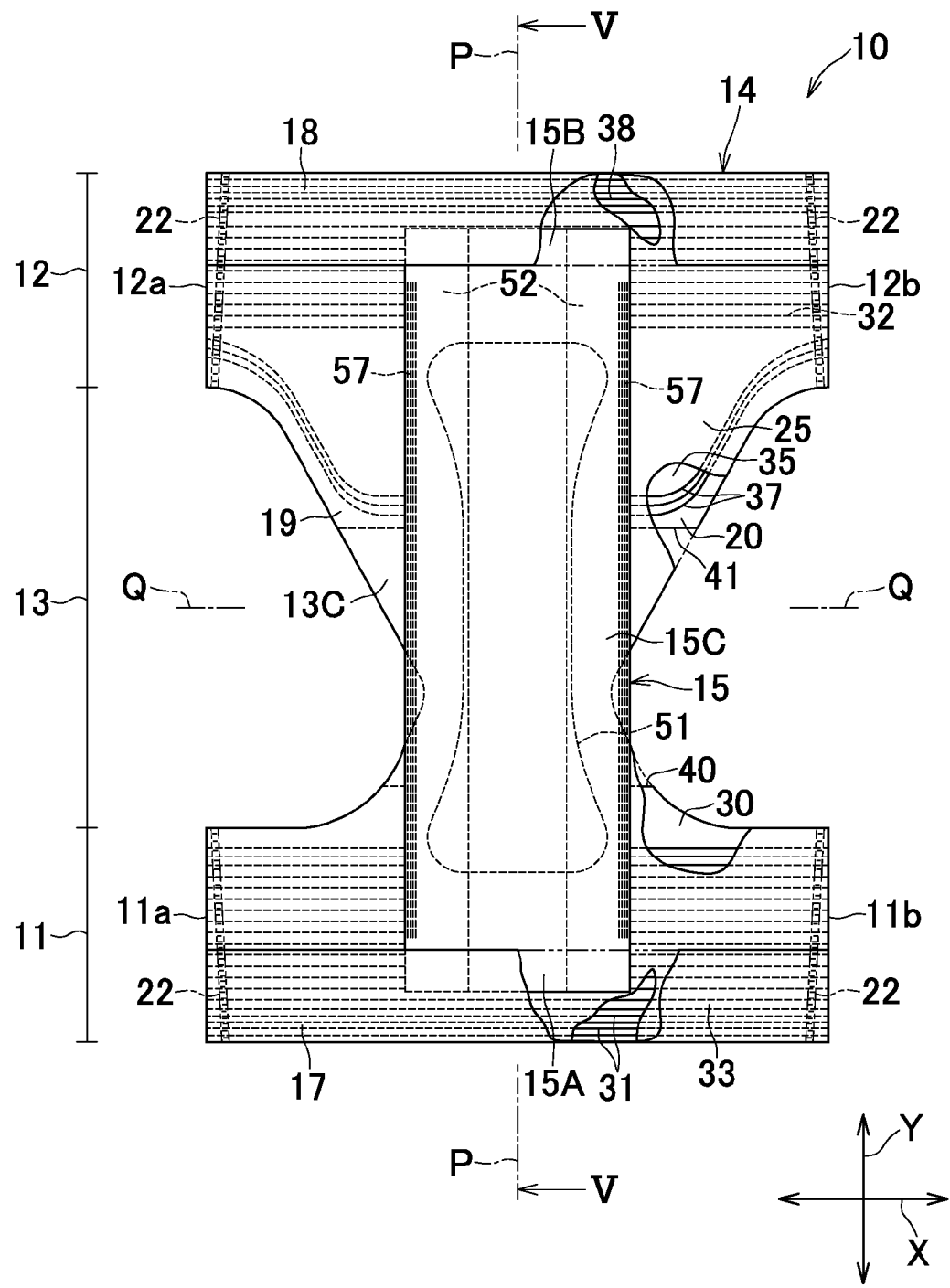
FIG. 2 is a partially cutaway developed plan view of the diaper.
Figure 3:
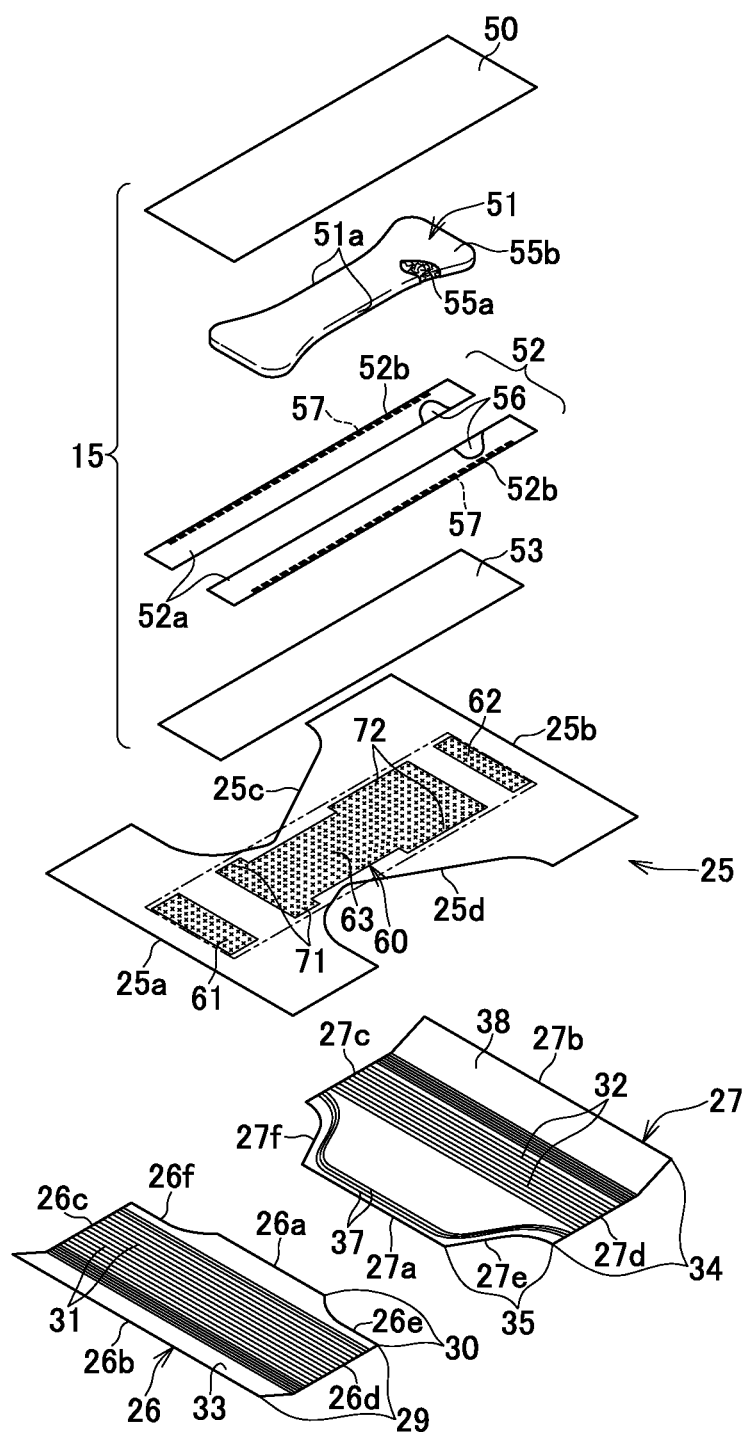
FIG. 3 is an exploded perspective view of the diaper.

Referring to FIGS. 1 through 3, a disposable pants-type diaper 10 as one example of the pants-type wearing article according to the present invention has a transverse direction X and a longitudinal direction Y and includes a skin-facing surface, a non-skin-facing surface opposite to the skin-facing surface, a front waist region 11, a rear waist region 12, a crotch region 13 extending between the front waist region 11 and the rear waist region 12, a chassis 14 defining a basic form of the diaper 10, and liquid-absorbent structure 15 lying on the skin-facing surface of the chassis 14 so as to extend across the crotch region 13 in the longitudinal direction Y. The diaper 10 further has an imaginary longitudinal center line P-P (referred to hereunder also as a longitudinal axis P) and an imaginary transverse center line Q-Q and is shaped substantially symmetrically about the imaginary longitudinal center line P-P. In FIG. 2, respective elastics to be described later in detail are illustrated in a state stretched against contractile force thereof.

The diaper 10 has, in addition, front and rear ends 17, 18 both extending in the transverse direction X and lateral edges 19, 20 which are symmetric about the longitudinal axis P and opposite to each other in the transverse direction X. The lateral edges 19, 20 are shaped to be concave in the crotch region 13 so as to be put in close contact with inner sides of the wearer's thighs and an area of a central segment 13C in the crotch region 13 close to the front waist region 11 has the narrowest width. Lateral edges 11a, 11b of the front waist region 11 and lateral edges 12a, 12b of the rear waist region 12 opposed to each other in a front-back direction of the diaper 10 are joined together by a pair of side seams 22 extending in the longitudinal direction Y and thereupon a waist-opening and a pair of leg-openings 24 are formed. Along the side seams 22, the sheets overlapping each other are continually welded by heat- or ultrasonic-embossing techniques.

The chassis 14 includes a base sheet 25 formed of a fibrous nonwoven fabric lying on the skin-facing surface so as to define the front and rear waist regions 11, 12 and the crotch region 13 in a continuous fashion and front and rear waist sheets 26, 27 formed of a fibrous nonwoven fabric lying on the non-skin-facing surface so as to be spaced apart from and opposite to each other in the longitudinal direction Y.

The base sheet 25 has first and second ends 25a, 25b spaced apart from and opposite to each other in the longitudinal direction Y and lateral edges 25c, 25d spaced apart from and opposite to each other in the transverse direction X. The lateral edges 25c, 25d include rectilinear segments in the front and rear waist regions 11, 12 and curved segments concaved toward the longitudinal axis P more deeply on the side of the front waist region 11 than on the side of the rear waist region 12.

The front waist sheet 26 is a substantially trapezoidal sheet defining the front waist region 11 and part of the crotch region 13 and contoured by an intermediate inner end 26a and an outer end 26b extending in the transverse direction X, outer lateral edges 26c, 26d extending in the longitudinal direction Y, and inner ends 26e, 26f by the intermediary of which the outer lateral edges 26c, 26d are connected to the intermediate inner end 26a. The inner ends 26e, 26f respectively have rectilinear segments extending from the associated outer lateral edges 26c, 26d in the transverse direction X and curved segments extending from the respective rectilinear segments to the intermediate inner end 26a. The front waist sheet 26 has a rectangular main part 29 extending in the transverse direction X between the lateral edges 26c, 26d and an extension segment 30 which is narrower than the main part 29 and extends between the inner ends 26e, 26f.

Between the main part 29 of the front waist sheet 26 and the base sheet 25, a plurality of first waist elastics (waist elastics) 31 extending in the transverse direction between the lateral edges 26c, 26d are contractibly attached under tension. A folded portion 33 is defined between an outermost one of the first waist elastics 31 lying on the main part 29 in the longitudinal direction Y and the outer end 26b. The folded portion 33 is adapted to be folded along the first end 25a of the base sheet 25 having been provided on its inner surface with the liquid-absorbent structure 15 and then to be secured to the skin-facing surface of the base sheet 25 and the liquid-absorbent structure 15.

The rear waist sheet 27 is a substantially trapezoidal sheet defining the rear waist region 12 and part of the crotch region 13 and contoured by an intermediate inner end 27a and an outer end 27b extending in the transverse direction X, outer lateral edges 27c, 27d extending from the outer end 27b in the longitudinal direction Y, and curved lateral inner ends 27e, 27f by the intermediary of which the outer lateral edges 27c, 27d are connected to the intermediate inner end 27a. The rear waist sheet 27 has a rectangular main part 34 extending in the transverse direction X between the lateral edges 27c, 27d and a substantially trapezoidal extension segment 35 which is narrower than the main part 34 and extends between the lateral inner ends 27e, 27f.

Between the main part 34 of the rear waist sheet 27 and the base sheet 25, a plurality of second waist elastics (waist elastics) 32 extending in the transverse direction X are contractibly attached under tension. A folded portion 38 is defined between an outermost one of the second waist elastics 32 lying on the main part 34 and the outer end 27b in the longitudinal direction Y. The folded portion 38 is adapted to be folded along the second end 25b of the base sheet 25 previously having been provided on its inner surface with the liquid-absorbent structure 15 and then to be secured to the skin-facing surface of the base sheet 25 and the liquid-absorbent structure 15.

Between the extension segment 35 of the rear waist sheet 27 and the base sheet 25, a plurality of leg-elastics 37 extending from respective rear halves of peripheries of the leg-openings, i.e., from respective lower ends of the outer lateral edges 27c, 27d of the rear waist sheet 27 in a curved state along the lateral inner ends 27e, 27f through the crotch region 13 to a lower end of the intermediate inner end 27a are contractibly attached under tension.

Figure 4:
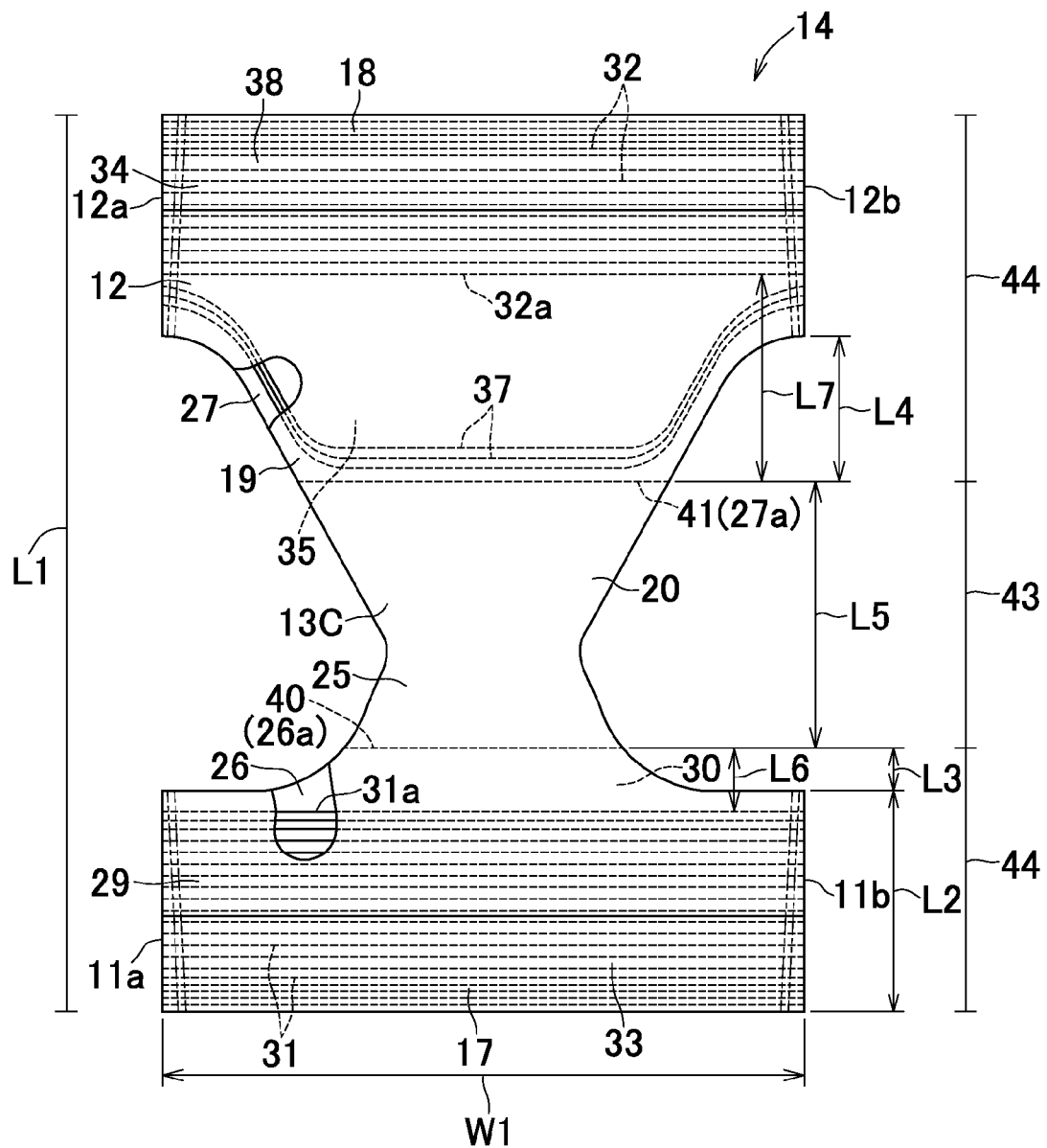
FIG. 4 is a plan view of the chassis.

Referring to FIGS. 3 and 4, the intermediate inner ends 26a, 27a respectively lie in the crotch region 13 of the chassis 14 which is, as has previously been described, composed of the base sheet 25 and the front and rear waist sheets 26, 27 layered and secured to predetermined front and rear regions. These intermediate inner ends 26a, 27a lying in these regions respectively define first and second boundaries 40, 41 respectively sectionalize zones in which the front and rear waist sheets and segments of the base sheet 25 defining the front and rear waist region and a zone composed of only the base sheet 25 are layered and extending between the front and rear waist sheets. In other words, the chassis 14 is divided into a monolayer zone 43 extending between the first and second boundaries 40, 41 (corresponding to the central segment 13C of the crotch region 13) and formed of the base sheet 25 alone and multilayer zones 44 respectively extending outboard of the first and second boundaries 40, 41 in the longitudinal direction Y and composed of the base sheet 25 and the front and rear waist sheets 26, 27. Taking account of the fact that the monolayer zone 43 and the multilayer zones 44 include the common base sheet 25 and the multilayer zones 44 are formed of the base sheet 25 extending over the diaper 10 as a whole, it will be understood that the multilayer zones 44 have a sheet strength higher than that of the monolayer zone 43. Thus, there is a likelihood that the tensile stress might be concentrated along the first and second boundaries 40, 41 when the chassis 14 is pulled with a relatively strong force in the longitudinal direction Y and the diaper 10 might be broken along these boundaries 40, 41.

As just described, the central segment 13C in the crotch region 13 of the chassis 14 is the monolayer zone 43 and more flexible than the multilayer zones 44. As a result, during use of the diaper 10, the central segment 13C is easily deformed between the wearer's thighs whereby the feeling to wear should not be deteriorated and, in addition, usage of material is smaller than where the crotch region 13 is entirely covered with the front and rear waist sheets 26, 27 and thereby saving manufacturing costs. In an embodiment of the diaper 10 including the front and rear waist regions 11, 12 and the crotch region 13 respectively formed of separate sheet members, the diaper 10 might be broken in vicinities of the boundaries between the front and rear waist regions and the crotch region along which these sheet members are joined to each other, for example, when the diaper 10 is pulled in a vertical direction to put on. However, according to the present invention, the base sheet 25 defining the chassis 14 has a shape which continuously extends over the front and rear waist regions 11, 12 and the crotch region 13 and thereby can avoid such disadvantageous situation.

Now respective dimensions of the diaper 10 (corresponding to the respective dimensions of the chassis 14) will be described hereunder. A dimension L1 of the diaper 10 in the longitudinal direction Y is in a range of about 600 to about 1000 mm, a dimension W1 thereof in the transverse direction X is in a range of about 400 to about 800 mm, a dimension L2 of the lateral edges 11a, 11b of the front waist region 11 in the longitudinal direction Y (equal to the dimension of the lateral edges 12a, 12b of the rear waist region 12 in the longitudinal direction Y) is in a range of about 80 to about 150 mm, a dimension L3 of the extension segment 30 of the front waist sheet 26 in the longitudinal direction Y is in a range of about 20 to about 60 mm, a dimension L4 of the extension segment 35 of the rear waist sheet 27 in the longitudinal direction Y is in a range of 60 to 100 mm, and a distance dimension in the longitudinal direction Y between the first and second boundaries 40, 41, i.e., a dimension L5 of the monolayer zone 43 in the longitudinal direction is in a range of about 40 to about 290 mm, preferably in a range of about 220 to about 260 mm. To ensure that an advantageous effect of the present invention described later, the dimensions L3, L4 of the extension segments 30, 35 in the longitudinal direction Y are about 30 mm or larger.

As has previously been described, the extension segment 35 is larger than the extension segment 30 in the illustrated embodiment but this relationship may be vice versa or both extension segments 30, 35 may have the same size. In this regard, taking account of a likelihood that the crotch region 13 might be partially broken rather on the side of the rear waist region 12 than on the side of the front waist region 11, for example, when the diaper 10 is put on the aged wearer in a sitting posture as will be described in more detail later, the extension segment 35 is preferably larger than the extension segment 30 and the multilayer zone 44 is preferably formed in the crotch region 13 on the side of the rear waist region 12 over a range as large as possible.

As a material of the base sheet 25 and the front and rear waist sheets 26, 27, for example, at least one of a spunbonded fibrous nonwoven fabric, an SMS (spunbonded/meltblown/spunbonded) fibrous nonwoven fabric, an airthrough fibrous nonwoven fabric, a plastic sheet and a laminate thereof, each having a mass per unit area in a range of about 10 to about 40 g/m$^2$ and a fiber density in a range of about 0.03 to about 0.10 g/cm$^3$ may be used. In the illustrated embodiment, as a material of the base sheet 25, an SMS fibrous nonwoven fabric having a mass per unit area in a range of about 12 to about 18 g/m$^2$, preferably having amass per unit area of about 15 g/m$^2$ is used and as a material of the front and rear waist sheets 26, 27, a spunbonded fibrous nonwoven fabric having a mass per unit area in a range of about 14 to about 20 g/m², preferably having a mass per unit area of about 17 g/m².

When the base sheet 25 and the front and rear waist sheets 26, 27 are formed of a fibrous nonwoven fabric, in at least one of the base sheet 25 and the front waist sheet 26 or in at least one of the base sheet 25 and the rear waist sheet 27, most of component fibers are preferably oriented substantially in coincidence with the longitudinal direction Y of the diaper 10 or a percentage of the component fibers oriented substantially in coincidence with the longitudinal direction Y of the diaper 10 is preferably higher than the component fibers oriented not in coincidence with the longitudinal direction Y of the diaper 10. Such countermeasure is effective to restrict a likelihood that the peripheries of the leg-openings might be partially broken along the first and second boundaries extending in the transverse direction X.

While the folded portions 33, 38 of the front and rear waist sheets 26, 27 are formed of the same material as that of the main parts 29, 34 in the illustrated embodiment, it is possible to form these folded portions 33, 38 from separately prepared sheet material and to secure them to the skin-facing surface of the main parts 29, 34. It is also possible to form the front and rear waist sheets 26, 27 from a single sheet material having the same shape as the base sheet 25 defining a basic shape of the diaper 10 and to form the base sheet 25 from a pair of sheet members respectively having the same shapes as the front and rear waist sheets 26, 27. Even in this case, the central segment 13C in the crotch region 13 is the monolayer zone 43 adapted to assure an advantageous effect of the present invention described later in detail.

As the first and second waist elastics 31, 32, for example, string or strand elastics each having a fineness in a range of about 470 to about 1240 dtex and an elongation ratio in a range of about 1.5 to about 3.5 may be used. The fineness as well as the elongation ratio thereof are not limited to the above ranges but may be appropriately selected. In the illustrated embodiment, as the first and second waist elastics 31, 32, from the side of the crotch region 13, two elastics each having a fineness of about 620 dtex, nine elastics each having a fineness of about 780 dtex, four elastics each having a fineness of about 470 dtex are arranged at substantially the same intervals (pitches) and, in addition to them, ten elastics each having a fineness of about 940 dtex at pitches smaller than the pitches for the precedent elastics.

As each set of the leg-elastics 37, a plurality of elastic yarns or threads having a fineness in a range of about 500 to about 800 dtex, preferably having a fineness of about 620 dtex are arranged and, depending on the stiffness of the base sheet 25 and front and rear waist sheets 26, 27, assuming that these sheets are formed of a fibrous nonwoven fabric as widely used in the relevant technical field, an elongation ratio of the leg-elastics 37 in the segments (rectilinear segments) thereof overlapping the liquid-absorbent structure 15 and rectilinearly extending in the transverse direction X along the inner end 27a of the rear waist sheet 27 is in a range of about 1.0 to about 2.0, preferably about 1.4 and an elongation ratio in the segments extending along the lateral inner ends 27e, 27f of the rear waist sheet 27 (oblique segments) is in a range of about 2.0 to about 2.5, preferably about 2.3. The elongation ratio of the leg-elastics 37 may be set to be lower than the elongation ratio of the oblique segments in this manner to inhibit a likelihood that the liquid-absorbent structure 15 might be deformed under contraction of the leg-elastics 37 and the liquid-absorption capacity thereof might be deteriorated.

As illustrated in FIG. 4, the interval (pitch) between each pair of the adjacent elastics in the first and second waist elastics 31, 32, respectively, arranged in the front and rear waist regions 11, 12 is smaller than both a dimension L6 in the longitudinal direction Y from an innermost elastic 31a to the first boundary 40 and a dimension L7 in the longitudinal direction Y from an innermost elastic 32a to the second boundary 41. Specifically, the pitch of the first and second waist elastics 31, 32 is in a range of about 6.0 to about 10.0 mm, the dimension L6 is in a range of about 30.0 to about 80.0 mm and the dimension L is in a range of about 90.0 to about 150.0 mm. In consequence, a stiffness of the front and rear waist regions in each portion defined between each pair of the adjacent elastics of the first and second waist elastics 31, 32 is higher than a stiffness in the portions of the front and rear waist regions extending downward from the respective innermost elastics 31a, 32a. This means that, for example, even when the wearer bends forward and, as a result, the front waist region 11 is folded and the region extending downward from the elastic 31a is significantly folded to form noticeable gathers, none of noticeable gather is developed in the portion defined between each pair of the adjacent first waist elastics 31. In this way, the stretching properties of the elastic zone defined by the first waist elastics 31 should not be limited.

In the portion of the crotch region 13 near to the front waist region 11 of the diaper 10 according to the illustrated embodiment, the leg-elastics 37 are not arranged between the base sheet 25 and the extension segment 30 of the front waist sheet 26 and arranged only the portion of the crotch region 13 close to the rear waist region 12. As a result, the portion of the crotch region 13 close to the front waist region 11 is not formed with gathers or substantially not formed with gathers. Consequently, a possibility of developing the gathers catching the wearer's legs can be inhibited and therefore a possibility that the wearer's skin might be irritated due to contact of the wearer's thighs with such gathers is also inhibited.

Referring to FIGS. 2 and 3, the liquid-absorbent structure 15 includes a front end portion 15A, a rear end portion 15B and a central portion 15C extending between the front and rear end portions 15A, 15B. The liquid-absorbent structure 15 lies on the skin-facing surface and has a body side liner 50 formed of a liquid-permeable fibrous nonwoven fabric, an absorbent core 51 having a pair of concave lateral edges 51a, a pair of containment sheets 52 and a leakage barrier sheet 53. The absorbent core 51 includes a core material 55a formed of a mixture of fluff pulp having a mass per unit area in a range of about 0 to about 500 g/m² and absorbent polymer particles or the like, and a liquid-absorbent and diffusive core wrapping sheet 55b such as tissue paper adapted to wrap the core material 55a as a whole. The containment sheets 52 are provided on inner surfaces thereof with elongate liquid-impermeable leakage barrier films 56.

The paired containment sheets 52 are spaced apart from each other in the transverse direction X and each of the containment sheets 52 has a proximal edge 52a secured between the absorbent core 51 and the associated leakage barrier sheet 53 and a distal edge 52b lying outboard of the leakage barrier sheet 53 as viewed in the transverse direction X and extending in the longitudinal direction Y. Within the distal edge 52b, elastics 57 are contractibly attached under tension. Upon contraction of the elastic 57, the distal edge 52b is spaced away from the body side liner 50 toward the wearer's body and comes in close contact with the wearer's thighs to prevent leakage of body waste. The leakage barrier sheet 53 is formed of at least one of a liquid-impermeable fibrous nonwoven fabric, a liquid-impermeable but breathable plastic film and a laminate thereof and arranged so that at least a substantially entire lower surface of the absorbent core 51 may be covered with the leakage barrier sheet 53 to prevent bodily fluids from leaking through the non-skin-facing surface (bottom surface) of the liquid-absorbent structure 15.

Figure 5:
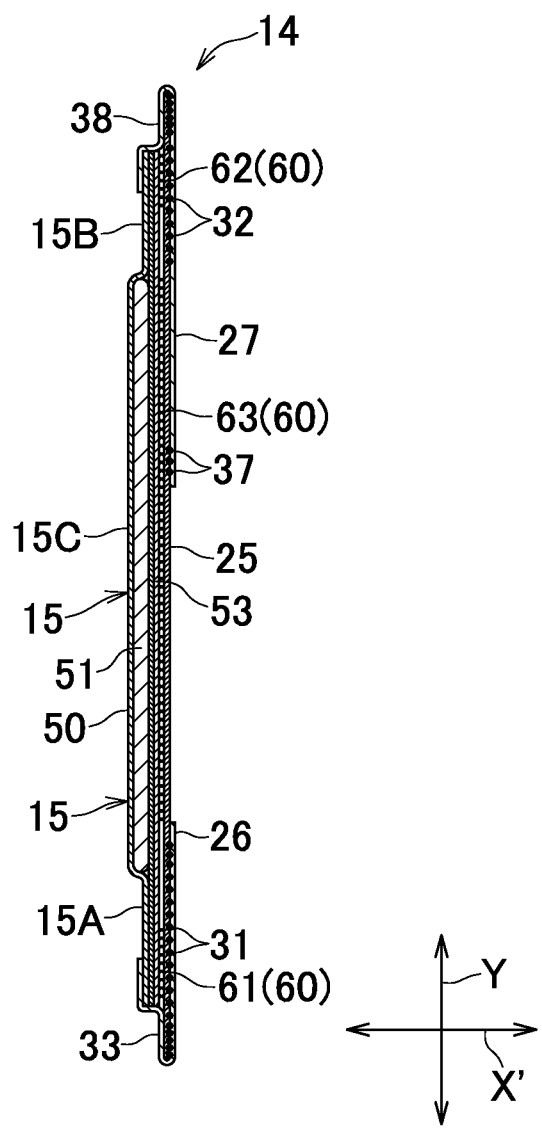
FIG. 5 is a schematic sectional view taken along line V-V in FIG. 2.
Figure 6:
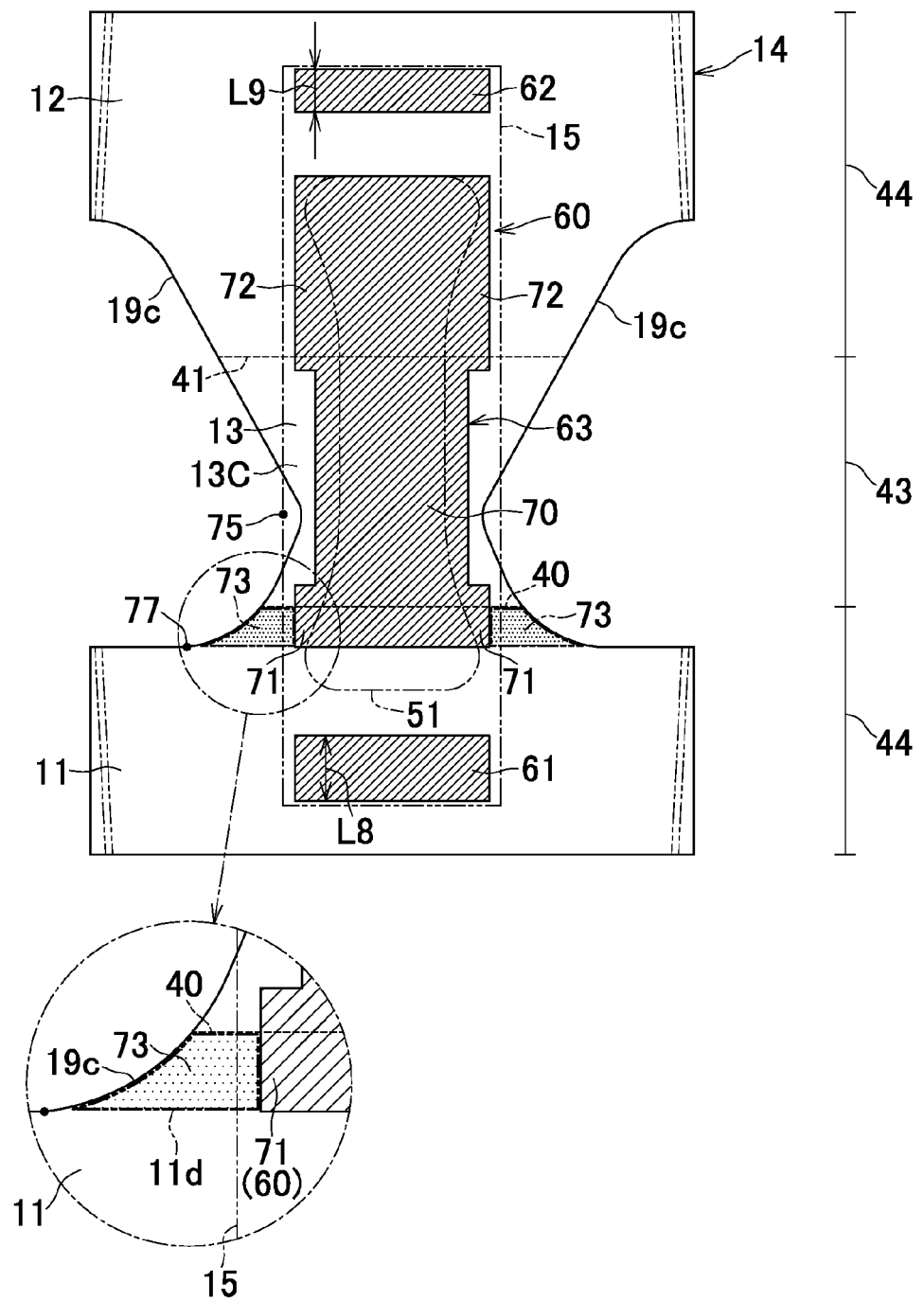
FIG. 6 is a developed plan view of the diaper wherein only an outer shape of the diaper and joint regions are indicated by solid lines and joint patterns within the respective joint regions are also indicated.

Referring to FIGS. 3 and 5, the liquid-absorbent structure 15 and the chassis 14 (the base sheet 25) are affixed to each other by the intermediary of a joint region 60 formed of a known joining means such as a hot melt adhesive applied to at least one of opposing surfaces of the liquid-absorbent structure 15 and the chassis 14 (the base sheet 25). The joint region 60 includes a front end joint region 61 in which the front end portion 15A of the liquid-absorbent structure 15 is secured to the inner surface of the chassis 14, a rear end joint region 62 in which the rear end portion 15B of the liquid-absorbent structure 15 is secured to the inner surface of the chassis 14 and an intermediate joint region 63 defined between the first and rear end joint regions 61, 62 and in which the central portion 15C of the liquid-absorbent structure 15 is affixed to the inner surface of the chassis 14.

The intermediate joint region 63 is spaced apart from the front and rear end joint regions 61, 62 in the longitudinal direction Y by predetermined dimensions and includes a substantially rectangular central joint region 70 extending from the portion of the crotch region 13 close to the front waist region 11 to the lower end of the rear waist region 12, first lateral joint regions 71 lying outboard of the central joint region 70 as viewed in the transverse direction X in the portion of the crotch region 13 close to the front waist region 11 and extending in the longitudinal direction Y, and second lateral joint regions 72 lying outboard of the central joint region 70 as viewed in the transverse direction X in the portion of the crotch region 13 close to the rear waist region 12. The first and second lateral joint regions 71, 72 are continuous with the central joint region 70 in the transverse direction X in such a manner that the first boundary 40 extends across the first lateral joint regions 71 and the second boundary 41 extends across the second lateral joint regions 72. The description used herein "the first boundary 40 extends across the first lateral joint regions 71" means that, within the first lateral joint regions 71 (joint region 60), the first lateral joint regions 71 directly or indirectly overlap the boundary 40 in a thickness direction of the diaper 10 and the description used herein "the second boundary 41 extends across the second lateral joint regions 72" similarly means that, within the second lateral joint regions 72, the second lateral joint regions 72 directly or indirectly overlap the boundary 41 in the thickness direction of the diaper 10.

The front and rear end joint regions 61, 62 are provided for the purpose of stably affixing the liquid-absorbent structure 15 to the multilayer zone 44 of the chassis 14 and therefore these joint regions preferably have the desired dimensions in the longitudinal direction Y, specifically, dimensions L8, L9 of the front and rear end joint regions 61, 62 in the longitudinal direction Y are in a range of about 10 to about 100 mm, preferably in a range of about 30 to about 80 mm. In the illustrated embodiment, the dimension L8 of the front end joint region 61 in the longitudinal direction Y is about 60 mm and the dimension L9 of the rear end joint region 62 in the longitudinal direction Y is about 40 mm, namely, the dimension L8 is larger than the dimension L9. However, the dimension L9 may be larger than the dimension L8 or these two dimensions L8, L9 may be substantially the same as long as the liquid-absorbent structure 15 can be stably affixed.

In parts of the peripheries of the respective leg-openings, more specifically, in portions of the crotch region 13 close to the front waist region 11, corners 73 (flap-like portions) formed of the multilayer zone 44 are defined between the first lateral joint regions 71 and the concave lateral edges of the crotch region 13. A dimension of the corners 73 in the longitudinal direction Y is the same as the dimension L3 in the longitudinal direction Y of the extension segment 30 of the front waist sheet 26 and preferably at least about 30 mm or more.

Figure 7:
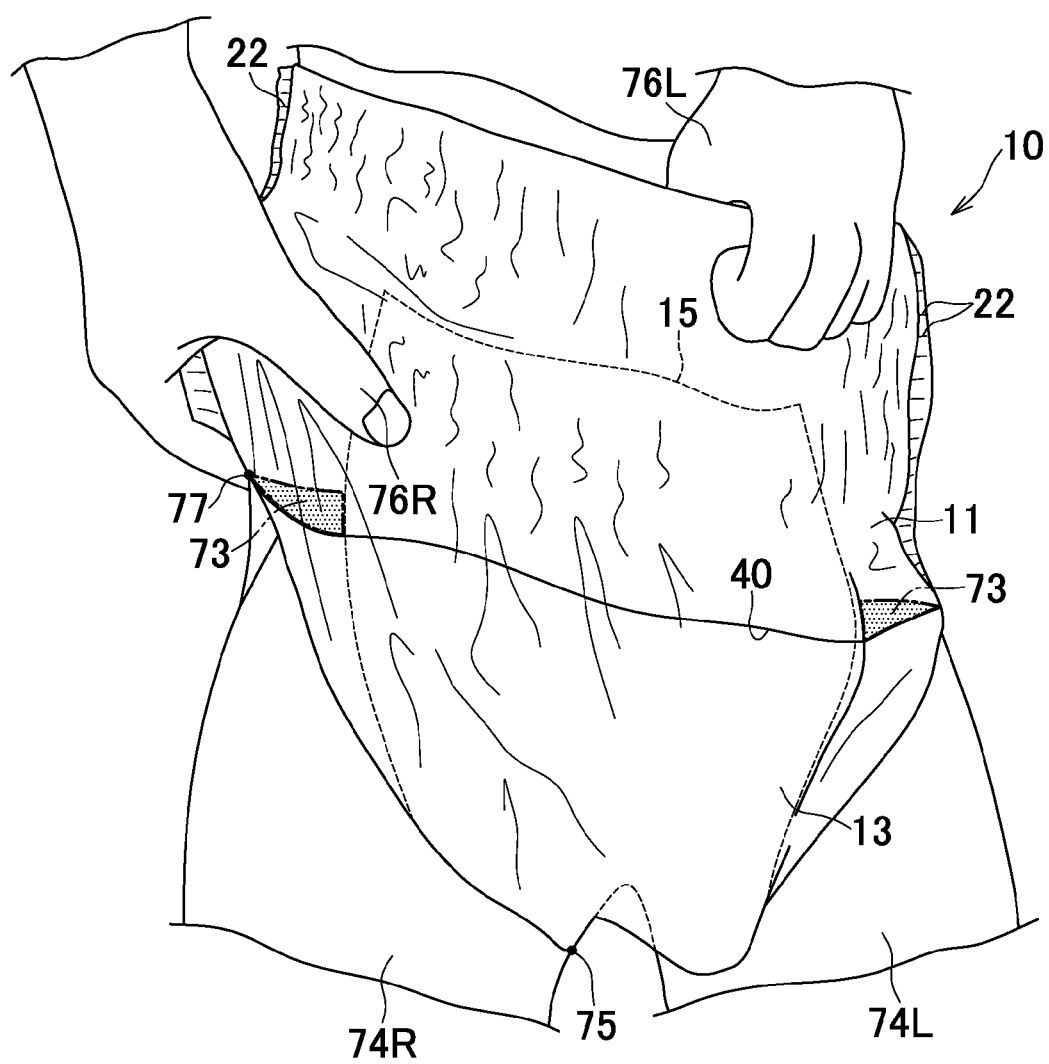
FIG. 7 is the diaper put on the wearer's body as viewed from the front side.

Referring to FIG. 7, when the diaper 10 is put on, for example, an aged person for whom it is difficult to support the body on one foot, it is necessary for the wearer or a care person to insert the wearer's legs 74L, 74R into the leg-openings 24 and then to lift a portion of the wearer's buttocks corresponding to one leg with a remaining portion of the buttocks corresponding to the other leg placed on the floor or the seat of a chair in order that the diaper 10 can be pulled up one side by one side to put the diaper 10 on the proper position. In this case, the aged wearer often holds the front waist region 11 or the lateral portions of the diaper 10 in vicinities of the seams 22 since the aged wearer is often humpbacked and cannot smoothly extend the left hand toward the back.

After the side of the diaper 10 associated with the leg 74L has been pulled up, the portion of the buttocks at the side associated with the leg 74R is lifted and the diaper 10 is pulled up with the portion of the buttocks associated with the leg 74L kept in contact with the seat of the chair. In this posture of the wearer, the rear waist region 12 of the diaper 10 associated with the leg 74L is pressed against the seat of the chair under the wearer's own weight. If the wearer holds the front waist region 11 or the lateral portion and pulls up the diaper 10 in this situation, a region 75 of the liquid-absorbent structure 15 intersecting with the leg-opening 24 is put in contact with the inner side of the wearer's thigh as being caught thereby and, in consequence, the leg-opening periphery is pulled in the longitudinal direction between the region 75 and the wearer's right hand 76R. When the front waist region 11 as a whole and the leg-opening periphery are subjected to the tensile stress functioning to pull them in the longitudinal direction, if the inner end of the front waist region 11 and the lateral edges of the crotch region 13 are orthogonal to each other, the tensile stress will be concentrated into a region 77 apt to be remarkably deformed and eventually there is a likelihood that the leg-opening periphery might be partially broken.

Even when the diaper 10 is put on an aged wearer who is able to support the body on one foot or an infant wearer in a standing posture, if the wearer's body slightly wet, for example, immediately after the wearer had a bath, the front and rear waist regions 11, 12 stick to the wearer's skin increasing frictional heat and it becomes difficult to pull up the diaper 10 smoothly. In such a situation also, if the front waist region 11 is held and it is tried to pull up the diaper 10 forcibly, there is a likelihood that the leg-opening periphery might be partially broken.

However, the diaper 10 according to the present invention includes, in the portion of the crotch region 13 close to the front waist region 11, the corners 73 formed of the multilayer zone 44 and contoured by the inner end 11d of the front waist region 11, the lateral edges 19c of the crotch region 13, the first lateral joint regions 71 (joint region 60) and the first boundary 40. Consequently, the inner end 11d of the front waist region 11 is no more orthogonal to the lateral edges 19c of the crotch region 13 and rather gentle curves extend from the inner end 11d of the front waist region 11 to the lateral edges 19c of the crotch region 13. In this way, the tensile stress due to a remarkable deformation is not concentrated into any point and rather disconcentrated in the respective corners 73. Further, the first boundary 40 lies inboard of the portion 77 in which the inner end 11d of the front waist region 11 intersects with the curved lateral edges 19c of the crotch region 13, and in the vicinity of the portion 77, located is the multilayer zone 44 composed of the base sheet 25 and the front waist sheet 26. The multilayer zone 44 has a relatively high sheet strength and a correspondingly high break resistance. Therefore, even if the wearer holds the front waist region 11 with the left hand 76L and pulls up this or the wearer holds the waist-opening periphery with the right hand 76R and pulls up this without taking account of the situation that the liquid-absorbent structure 15 is partially caught by the inner side of the leg 74R in the contact region 75, the corners 73 lying outboard of the lateral edges of the liquid-absorbent structure 15 should not be partially broken.

The arrangement such that the first boundary 40 extending in the transverse direction across the joint region 60 ensures the liquid-absorbent structure 15 to be affixed to the vicinity of the first boundary 40 and makes it possible to lessen a difference in degree of elongation percentage and deformation (variation in a tensile strength of a sheet) due to the number of sheets in the leg-opening periphery and thereby to prevent the sheets from being broken along or in the vicinity of the boundary 40. When the joint region 60 is located only in the monolayer zone 43, if body waste is discharged onto the inner surface of the liquid-absorbent structure 15 of the diaper put on the wearer's body, the monolayer zone 43 might be pulled downward under the own weight of the liquid-absorbent structure 15 and the monolayer zone 43 having a relatively low sheet strength might be partially broken. However, the first and second boundaries 40, 41 extend across the joint region 60 and, as a result, the multilayer zone 44 sufficiently shares the load to prevent the monolayer zone 43 from being partially broken.

In the illustrated embodiment, the first lateral joint regions 71 are spaced apart from the second lateral joint regions 72 by a given dimension and, in consequence, the liquid-absorbent structure 15 as a whole should not be pulled toward the rear waist region 12 in cooperation with the leg-elastics 37 and the absorbent core 51 should not be shortened or displaced. Further, while the central segment 13C in the crotch region 13 is monolayered and relatively flexible, the number of the joint regions in which the liquid-absorbent structure 15 is affixed may be kept to the minimum necessary to maintain the desired flexibility.

The arrangement such that the front and rear end joint regions 61, 62 are spaced apart from the intermediate joint region 63 ensures the liquid-absorbent structure 15 to conform to movements of the wearer's body more smoothly than where the front and rear joint regions are continuous with the intermediate joint region 63. Particularly in the front waist region 11, the front end portion lies outboard of the intermediate joint region 63 as viewed in the longitudinal direction Y but the liquid-absorbent structure 15 is not affixed to the chassis 14 between the intermediate joint region 63 and the front end joint region 61. With this arrangement, the contractile force of the first waist elastics 31 should not directly affect the front end portion of the absorbent core 51 and should not develop gathers causing the absorption capacity thereof to be deteriorated.

The portions of the crotch region 13 close to the front and rear waist regions 11, 12 and lying on front- and back-sides of the wearer are formed of the multilayer zone 44, respectively, and the permeability in these portions is lower than where these portions are formed of the monolayer zone 43. As a result, it is possible to prevent the wearer's skin from being visually recognized through the diaper 10 from outside.

<Tensile Strength Test>

To compare a break-resistance (tensile strength) of the crotch region 13 when the diaper 10 is pulled in the longitudinal direction Y according to the embodiment of the present invention and the diaper according to a comparative example, a test described hereunder was carried out.

EXAMPLE

For the diaper 10 according to the present invention used in the present test, an SMS nonwoven fabric having a mass per unit area of about 15.0 g/m$^2$ was used as a material of the base sheet 25, a spunbonded nonwoven fabric having a mass per unit area of about 17.0 g/m$^2$ was used as a material of the front waist sheet and a hot melt adhesive was used as a bonding means to form the joint region 60.

Comparative Example

The diaper used as the Comparative Example was similar to the Example in terms of the basic construction except the shape of the front waist sheet 26. Specifically, the front waist sheet 26 did not have the extension segment 30, the inner end 26a of the front waist sheet 26, i.e., the first boundary 40 rectilinearly extends in the transverse direction X integrally with the inner end of the front waist region 11, and the crotch region 13 as a whole was formed of the base sheet 25 alone. An SMS nonwoven fabric having a mass per unit area of about 15.0 g/m$^2$ was used as a material of the base sheet 25, a spunbonded nonwoven fabric having a mass per unit area was used as a material of the front waist sheet and a hot melt adhesive was used as a material of the bonding means to form the joint region 60.

<Test Method>

Figure 8:
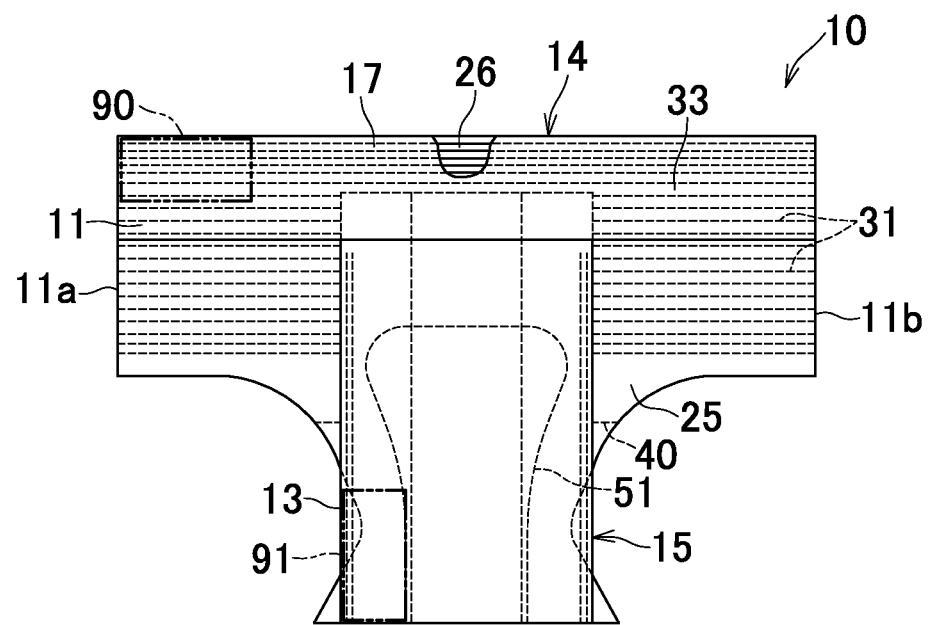
FIG. 8 is a plan view illustrating part of the diaper inclusive of the front waist region side used in a tensile strength test.
Figure 9:
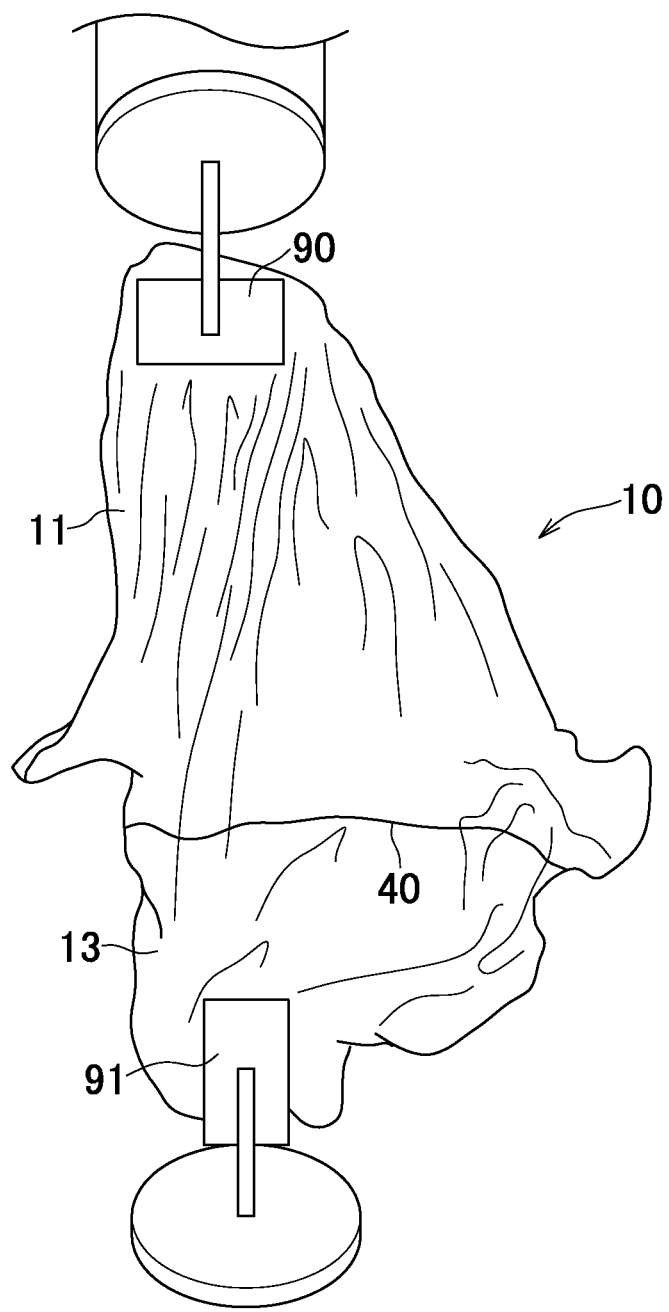
FIG. 9 FIG. 9 illustrates a test piece of the diaper being subjected to the tensile strength test.

For this test, AUTOGRAPH (Model AG-1kNI) manufactured by Shimadzu Corporation in Japan was used. The method of test will be described hereunder with reference to FIGS. 8 and 9. The front and rear waist regions 11, 12 were peeled off from each other at the seams 22 and the diaper 10 was cut along the imaginary transverse center line Q-Q to obtain a piece including the front waist region 11 used as a test piece. The test piece was held by a pair of chucks 90, 91. More specifically, a cantle at which the front end 17 and the lateral edge 11a of the front waist region 11 intersects each other was clamped by the chuck 90 and the region in which the portion of the liquid-absorbent structure 15 lying outboard of the absorbent core 51 as viewed in the transverse direction X overlaps the chassis 14 in the crotch region 13 was clamped by the chuck 91. A distance dimension between these two chucks 90, 91 was about 150 mm in the initial setting. The chuck 90 was moved away from the chuck 91 at a movement rate of about 500 mm/min so that the paired chucks 90, 91 may be gradually spaced away from each other until the diaper 10 began to be partially broken and a value of tensile stress (N) at this moment was measured. The test was repeated ten times for the respective diapers and the average value, the minimum value and the maximum value are indicated in TABLE 1.

TABLE 1

|  | Average Value (N) | Maximum Value (N) | Minimum Value (N) |
|---|---|---|---|
| Example | 68.4 | 74.0 | 61.8 |
| Comparative Example | 53.6 | 67.2 | 46.0 |

<Test Result>

As indicated in TABLE 1, all of the average value, the maximum value and the minimum value indicated by the Example are higher than those indicated by the Comparative Example, and from this test it was verified that the diaper 10 according to the Example is superior to the diaper according to the Comparative Example in the tensile strength as well as in the break-resistance.

The constituent members of the disposable diaper 10 as one example of the pants-type wearing articles according to the present invention are not limited to those described in the description but other types or kinds of materials widely used in the relevant technical field may be used without limitation and the terms "first" and "second" used in the description and Claims are used herein merely to distinguish similar elements or similar position.

The disclosure relating to the present invention as has been described above may be summarized in the aspects as will be described below.

A pants-type wearing article having a longitudinal direction and a transverse direction being orthogonal to the longitudinal direction, and including:

a skin-facing surface;

a non-skin-facing surface;

a front waist region;

a rear waist region;

a crotch region extending between the front and rear waist regions and having concave lateral edges;

a chassis defining the front and rear waist region and the crotch region; and a liquid-absorbent structure affixed to the skin-facing surface of the chassis and extending in the longitudinal direction at least in the crotch region, wherein:

the chassis includes a base sheet defining the front and rear waist regions and the crotch region and front and rear waist sheets spaced apart from each other in the longitudinal direction and defining together with the base sheet the front and rear waist regions;

the front and rear waist regions and at least a portion of the crotch region close to the front waist region define a multilayer zone composed of the base sheet and the front waist sheet layered with each other and a central segment of the crotch region defines a monolayer zone formed of the base sheet alone;

a boundary between the multilayer zone and the monolayer zone extends in the transverse direction; and the multilayer zone includes corners each surrounded by the boundary, an inner end of the front waist region, a joint region in which the liquid-absorbent structure is affixed to the chassis and the concave lateral edge of the crotch region, wherein the boundary extends across the joint region.

The present invention disclosed above may include at least the following embodiments:

(1) The joint region includes a central joint region extending in the longitudinal direction at least in the crotch region and a pair of first lateral joint regions lying outboard of the central joint region as viewed in the transverse direction and extending in the longitudinal direction in the portion of the crotch region close to the front waist region.

(2) The joint region includes the central joint region extending in the longitudinal direction at least in the crotch region and a pair of second lateral joint regions lying outboard of the central joint region as viewed in the transverse direction and extending in the longitudinal direction in the portion of the crotch region close to the rear waist region and the portion of the crotch region close to the rear waist region is the multilayer zone and the boundary between the multilayer zone and the monolayer zone extends across the joint region in the transverse direction.

(3) Each of the corners has a dimension in the longitudinal direction of at least about 30 mm.

(4) The joint region includes an intermediate joint region having, in turn, the central joint region and the first and second lateral joint regions, and front and rear end joint regions spaced apart from the intermediate joint region in the longitudinal direction and lying in the front and rear waist regions, respectively.

(5) The multilayer zone lying on the portion of the crotch region close to the rear waist region is provided with a plurality of leg-elastics include rectilinear segments extending in the transverse direction and intersect with the liquid-absorbent structure and curved segments lying on lateral portions of the rectilinear segments as viewed in the transverse direction and concavely extending along the lateral edges of the crotch region and wherein the rectilinear segments have an elongation ratio lower than that of the curved segments.

(6) Of the front and rear waist regions, at least the front waist region is provided with a plurality of waist elastics extending in the transverse direction and spaced apart from each other in the longitudinal direction and a distance dimension in the longitudinal direction from an innermost one of the waist elastics to the boundary is larger than a distance dimension between each pair of the adjacent waist elastics.

(7) At least one of the base sheet and the front and rear waist sheets is formed of a fibrous nonwoven fabric and component fibers of the fibrous nonwoven fabric are oriented in the longitudinal direction.

REFERENCE SIGNS LIST 10 disposable pants-type diaper (pants-type wearing article)
11 front waist region
12 rear waist region
13 crotch region
14 chassis
15 liquid-absorbent structure
25 base sheet
26 front waist sheet
27 rear waist sheet
31 first waist elastics (waist elastics)
32 second waist elastics (waist elastics)
37 leg-elastics
40 first boundary (boundary)
41 second boundary (boundary)
60 joint region
61 front end joint region
62 rear end joint region
63 intermediate joint region
70 central joint region
71 first lateral joint regions
72 second lateral joint regions
73 corners L3 dimension of extension segment of front waist sheet in longitudinal direction
X transverse direction
Y longitudinal direction

The invention claimed is:

1. A pants-type wearing article having a longitudinal direction and a transverse direction being orthogonal to the longitudinal direction, comprising:
   a chassis; and
   a liquid-absorbent structure,
   wherein:
   the chassis defines a front waist region, a rear waist region and a crotch region of the pants-type wearing article, said crotch region extending between the front and rear waist regions and having concave lateral edges,
   the chassis has a skin-facing surface and a non-skin-facing surface,
   the chassis is formed from:
      a base sheet defining the front and rear waist regions and the crotch region continuously in the longitudinal direction; and
      front and rear waist sheets spaced apart from each other in the longitudinal direction and defining together with the base sheet the front and rear waist regions;
   the chassis having:
      multilayer zones in the front and rear waist regions and at least a portion of the crotch region close to the front waist region, which multilayer zones are composed of the base sheet and the front and rear waist sheets layered with each other;
      a monolayer zone in a central segment of the crotch region which is formed of the base sheet alone, the base sheet alone forming the outermost non-skin-facing surface in the central segment of the crotch region; and
      a boundary between the multilayer zone and the monolayer zone extends in the transverse direction;
   the liquid-absorbent structure being affixed to the skin-facing surface of the chassis and extending in the longitudinal direction at least in the crotch region; and
   the multilayer zone includes corners each surrounded by the boundary, an intermediate inner end of the front waist region which is located between outer lateral edges of the front waist region extending in the longitudinal direction and extends partially toward the crotch region, a joint region in which the liquid-absorbent structure is bonded to the chassis and the concave lateral edge of the crotch region, wherein the boundary extends across the joint region.

2. The wearing article according to claim 1, wherein the joint region includes a central joint region extending in the longitudinal direction at least in the crotch region and a pair of first lateral joint regions lying outboard of the central joint region as viewed in the transverse direction and extending in the longitudinal direction in the portion of the crotch region close to the front waist region.

3. The wearing article according to claim 2, wherein the joint region includes the central joint region extending in the longitudinal direction at least in the crotch region and a pair of second lateral joint regions lying outboard of the central joint region as viewed in the transverse direction and extending in the longitudinal direction in the portion of the crotch region close to the rear waist region and the portion of the crotch region close to the rear waist region is the multilayer zone and the boundary between the multilayer zone and the monolayer zone extends across the joint region in the transverse direction.

4. The wearing article according to claim 1, wherein each of the corners has a dimension in the longitudinal direction of at least about 30 mm.

5. The wearing article according to claim 3, wherein the joint region includes an intermediate joint region having, in turn, the central joint region and the first and second lateral joint regions, and front and rear end joint regions spaced apart from the intermediate joint region in the longitudinal direction and lying in the front and rear waist regions, respectively.

6. The wearing article according to claim 3, wherein the multilayer zone lying on the portion of the crotch region close to the rear waist region is provided with a plurality of leg-elastics include rectilinear segments extending in the transverse direction and intersect with the liquid-absorbent structure and curved segments lying on lateral portions of the rectilinear segments as viewed in the transverse direction and concavely extending along the lateral edges of the crotch region and wherein the rectilinear segments have an elongation ratio lower than that of the curved segments.

7. The wearing article according to claim 1, wherein, of the front and rear waist regions, at least the front waist region is provided with a plurality of waist elastics extending in the transverse direction and spaced apart from each other in the longitudinal direction and a distance dimension in the longitudinal direction from an innermost one of the waist elastics to the boundary is larger than a distance dimension between each pair of the adjacent waist elastics.

8. The wearing article according to claim 1, wherein at least one of the base sheet and the front and rear waist sheets is formed of a fibrous nonwoven fabric and component fibers of the fibrous nonwoven fabric are oriented in the longitudinal direction.

9. The wearing article according to claim 2, wherein the joint region includes the central joint region extending in the longitudinal direction at least in the crotch region and a pair of second lateral joint regions lying outboard of the central joint region as viewed in the transverse direction and extending in the longitudinal direction in the portion of the crotch region close to the rear waist region and the portion of the crotch region close to the rear waist region is the multilayer zone and the boundary between the multilayer zone and the monolayer zone extends across the joint region in the transverse direction.

10. The wearing article according to claim 2, wherein each of the corners has a dimension in the longitudinal direction of at least about 30 mm.

11. The wearing article according to claim 3, wherein each of the corners has a dimension in the longitudinal direction of at least about 30 mm.

12. The wearing article according to claim 9, wherein each of the corners has a dimension in the longitudinal direction of at least about 30 mm.

13. The wearing article according to claim 9, wherein the joint region includes an intermediate joint region having, in turn, the central joint region and the first and second lateral joint regions, and front and rear end joint regions spaced apart from the intermediate joint region in the longitudinal direction and lying in the front and rear waist regions, respectively.

14. The wearing article according to claim 4, wherein the joint region includes an intermediate joint region having, in turn, a central joint region and first and second lateral joint regions, and front and rear end joint regions spaced apart from the intermediate joint region in the longitudinal direction and lying in the front and rear waist regions, respectively.

15. The wearing article according to claim 10, wherein the joint region includes an intermediate joint region having, in turn, the central joint region and the first lateral joint regions and second lateral joint regions, and front and rear end joint regions spaced apart from the intermediate joint region in the longitudinal direction and lying in the front and rear waist regions, respectively.

16. The wearing article according to claim 11, wherein the joint region includes an intermediate joint region having, in turn, the central joint region and the first and second lateral joint regions, and front and rear end joint regions spaced apart from the intermediate joint region in the longitudinal direction and lying in the front and rear waist regions, respectively.

17. The wearing article according to claim 12, wherein the joint region includes an intermediate joint region having, in turn, the central joint region and the first and second lateral joint regions, and front and rear end joint regions spaced apart from the intermediate joint region in the longitudinal direction and lying in the front and rear waist regions, respectively.

18. The wearing article according to claim 9, wherein the multilayer zone overlays a portion of the crotch region close to the rear waist region and is provided with a plurality of leg-elastics include rectilinear segments extending in the transverse direction and intersect with the liquid-absorbent structure and curved segments lying on lateral portions of the rectilinear segments as viewed in the transverse direction and concavely extending along the lateral edges of the crotch region and wherein the rectilinear segments have an elongation ratio lower than that of the curved segments.

19. The wearing article according to claim 4, wherein the multilayer zone overlays a portion of the crotch region close to the rear waist region and is provided with a plurality of leg-elastics include rectilinear segments extending in the transverse direction and intersect with the liquid-absorbent structure and curved segments lying on lateral portions of the rectilinear segments as viewed in the transverse direction and concavely extending along the lateral edges of the crotch region and wherein the rectilinear segments have an elongation ratio lower than that of the curved segments.

20. The wearing article according to claim 11, wherein the multilayer zone lying on the portion of the crotch region close to the rear waist region is provided with a plurality of leg-elastics include rectilinear segments extending in the transverse direction and intersect with the liquid-absorbent structure and curved segments lying on lateral portions of the rectilinear segments as viewed in the transverse direction and concavely extending along the lateral edges of the crotch region and wherein the rectilinear segments have an elongation ratio lower than that of the curved segments.

* * * * *